(12) United States Patent
Blanchard

(10) Patent No.: US 12,245,963 B2
(45) Date of Patent: Mar. 11, 2025

(54) REMOVABLE ELBOW BRACE

(71) Applicant: Arkansas Children's, Inc., Little Rock, AR (US)

(72) Inventor: Samantha J. Blanchard, Fayetteville, AR (US)

(73) Assignee: Arkansas Children's, Inc., Little Rock, AR (US)

( * ) Notice: Subject to any disclaimer, the term of this patent is extended or adjusted under 35 U.S.C. 154(b) by 280 days.

(21) Appl. No.: 18/080,939

(22) Filed: Dec. 14, 2022

(65) Prior Publication Data

US 2023/0181347 A1 Jun. 15, 2023

Related U.S. Application Data

(60) Provisional application No. 63/289,344, filed on Dec. 14, 2021.

(51) Int. Cl.
*A61F 5/058* (2006.01)
*A61F 5/01* (2006.01)
*A61F 5/37* (2006.01)

(52) U.S. Cl.
CPC ........ *A61F 5/05858* (2013.01); *A61F 5/0102* (2013.01); *A61F 5/0118* (2013.01); *A61F 5/05866* (2013.01); *A61F 5/373* (2013.01); *A61F 2005/0167* (2013.01); *A61F 2005/0172* (2013.01)

(58) Field of Classification Search
CPC .... A61F 5/0102; A61F 5/0104; A61F 5/0118; A61F 5/013; A61F 5/058; A61F 5/05841; A61F 5/05858; A61F 5/373; A61F 5/0111; A61F 5/0113; A61F 5/0106; A61F 5/0123; A61F 5/0127; A61F 13/063; A61F 13/069; A61F 13/101
See application file for complete search history.

(56) References Cited

U.S. PATENT DOCUMENTS

| | | | | |
|---|---|---|---|---|
| 4,753,240 | A  * | 6/1988 | Sparks | A61F 7/02 602/14 |
| 8,007,454 | B1 * | 8/2011 | Zerr | A61F 5/0111 602/23 |
| 2005/0234374 | A1* | 10/2005 | Grim | A61F 5/05841 602/6 |
| 2008/0103423 | A1* | 5/2008 | Nieberding | A61F 5/0102 602/7 |
| 2013/0184627 | A1* | 7/2013 | Vedder | A61B 17/1739 602/20 |
| 2013/0296757 | A1* | 11/2013 | Kaphingst | A61F 5/013 602/20 |
| 2020/0390196 | A1* | 12/2020 | Manzato | A43C 11/14 |

OTHER PUBLICATIONS

Invention Evaluator Report, IP section, received Oct. 18, 2021.

* cited by examiner

*Primary Examiner* — Keri J Nelson

(57) ABSTRACT

A brace to protect an elbow during healing, particularly for pediatric applications, is constructed from multiple thermoformable parts. The thermoformable parts harden like a cast, fitting partially around the humerus and the forearm as well as covering the posterior aspect of the elbow. The thermoformable parts are held in place by straps that extend between the parts, cupping the humerus and forearm therebetween. The brace may be customizable to any shape and size to the wearer. The brace may be easily removed for comfort or for washing and then replaced to provide continued support.

16 Claims, 4 Drawing Sheets

REMOVABLE ELBOW BRACE

CROSS-REFERENCE TO RELATED APPLICATIONS

This application claims the benefit of U.S. provisional patent application No. 63/289,344, filed on Dec. 14, 2021. Such application is incorporated herein by reference in its entirety.

STATEMENT REGARDING FEDERALLY SPONSORED RESEARCH OR DEVELOPMENT

Not applicable.

BACKGROUND

Elbow fractures are a common medical issue, particularly within pediatrics, with one report providing an estimated annual presentation rate of 177.3 per 100,000 of the population. Supracondylar humeral fractures, in particular, constitute between 5.5-7.7% of all pediatric fractures, and 55-80% of pediatric elbow fractures. Lateral condyle fractures of the humerus have an incidence of 15-17%, while medial epicondyle fractures represent approximately 12%. Radial head and neck fractures make up 5%.

The braces currently on the market for pediatric elbow fractures generally provide no coverage of the elbow. The brace may, for example, consist of bands wrapping above and below the elbow, with struts extending between and connecting the bands. The struts may meet at an angle at the elbow. In some cases, the angle at which the struts meet may be varied on the device, or it may be set permanently. Another alternative is a flexible wrap, which may or may not cover the elbow but does not provide rigid support. A third alternative is a traditional cast. These traditional casts cover the elbow and provide rigid support, but they are not breathable, may cause skin breakdown, may cause pressure injuries, and may require expensive replacement if they become wet. Traditional casts cannot of course be removed for washing or other reasons. None of these braces adequately support occult fractures or minor elbow injuries while also preventing skin or pressure injuries, allowing air to reach the skin, and being impervious to moisture.

References mentioned in this background section are not admitted to be prior art with respect to the present invention.

SUMMARY

The present invention is directed to a brace that covers and protects the elbow during healing. In certain embodiments, the brace is constructed from a thermoformable material that hardens like a cast, fitting partially around the humerus and the forearm as well as covering the posterior aspect of the elbow, yet is also removable. Also unlike a traditional cast, the brace in certain embodiments is waterproof and breathable. The brace may be held in place by straps and/or fasteners that extend between the two sides, cupping the humerus and forearm therebetween. In certain embodiments, the brace may be formed at various angles at the elbow, including for example a ninety-degree angle at the elbow. The brace may be customizable to any shape and size to fit any wearer. Because the brace is removable, it may allow the patient maximum freedom of movement during healing, and thus may, for example, be removed in order to wash.

These and other features, objects and advantages of the present invention will become better understood from a consideration of the following detailed description of the preferred embodiments and appended claims in conjunction with the drawings as described following:

DRAWINGS

DETAILED DESCRIPTION

Before the present invention is described in further detail, it should be understood that the invention is not limited to the particular embodiments described, and that the terms used in describing the particular embodiments are for the purpose of describing those particular embodiments only, and are not intended to be limiting, since the scope of the present invention will be limited only by the claims.

Figure 1:
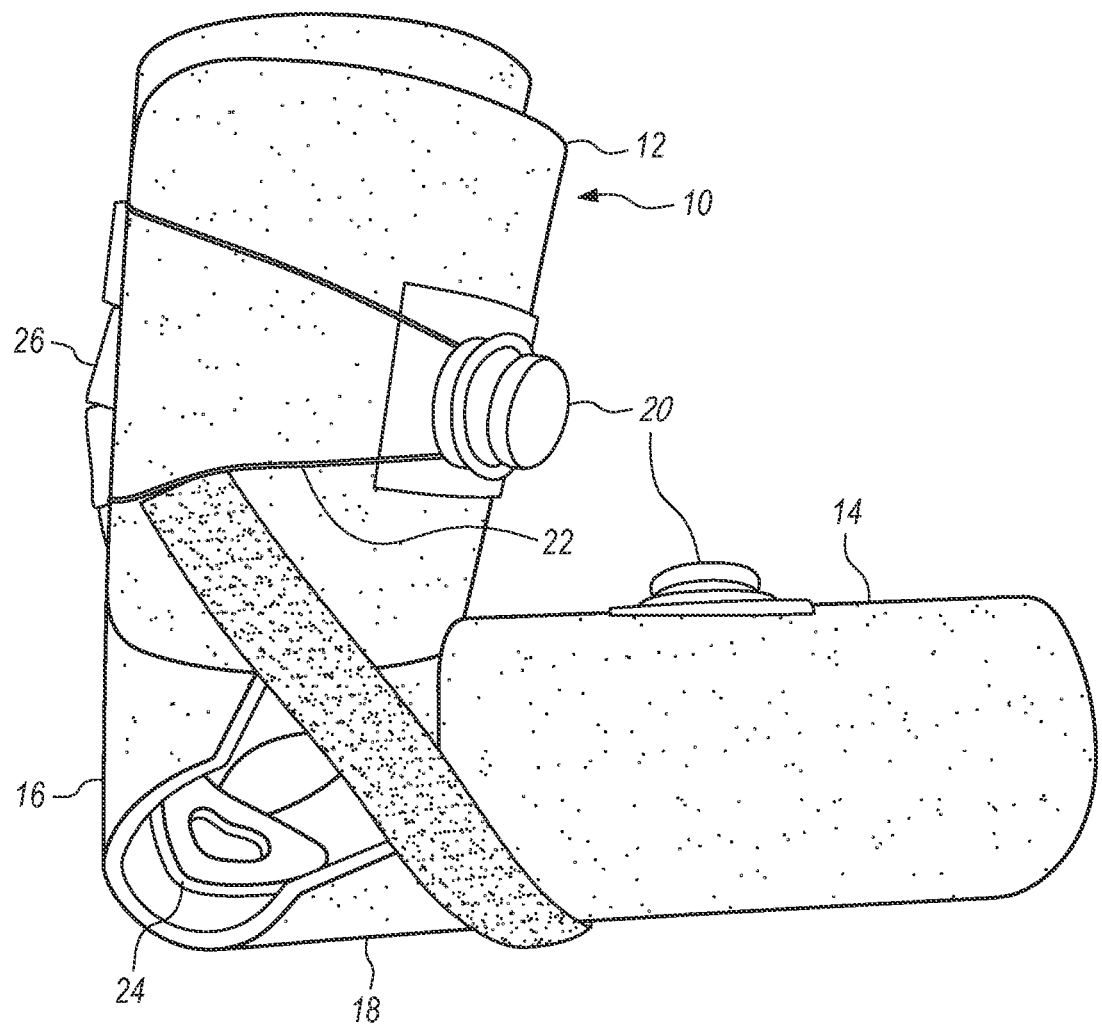
FIG. 1 is a right side elevational view of a first embodiment of the present invention.
Figure 2:
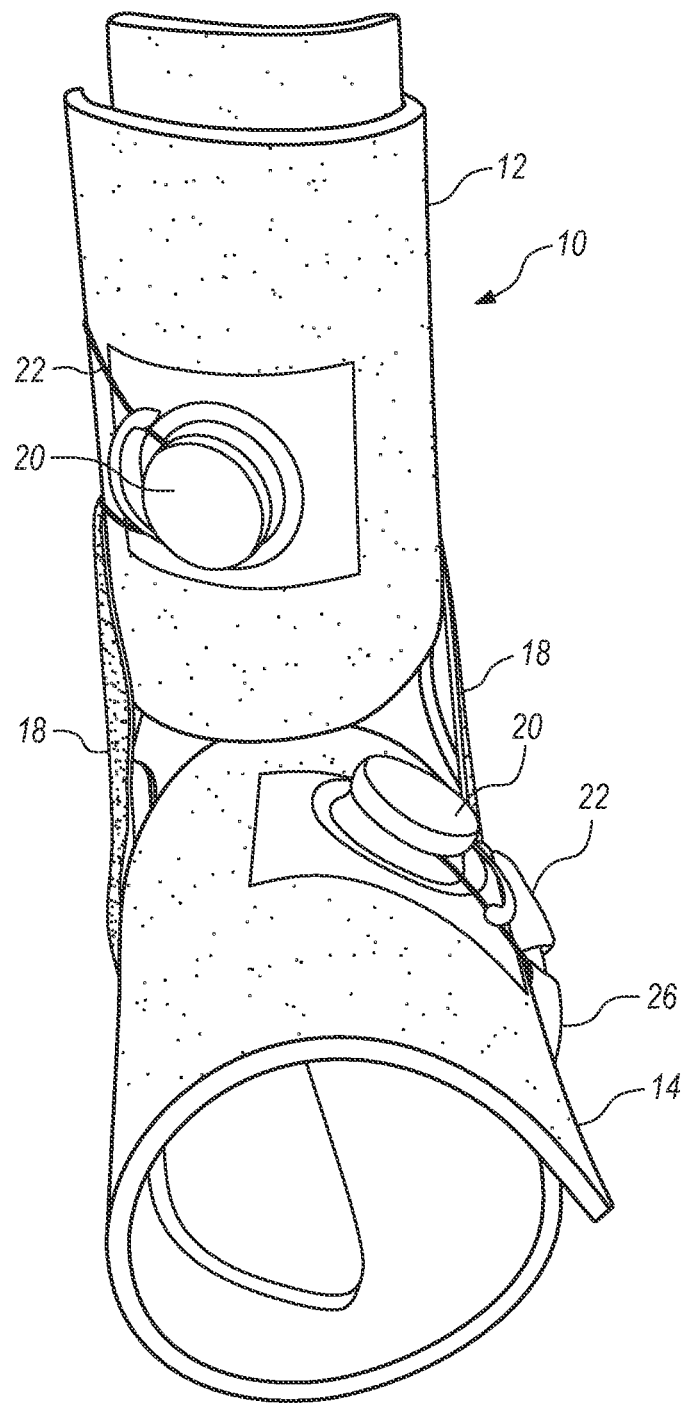
FIG. 2 is a front side elevational view of a first embodiment of the present invention.
Figure 3:
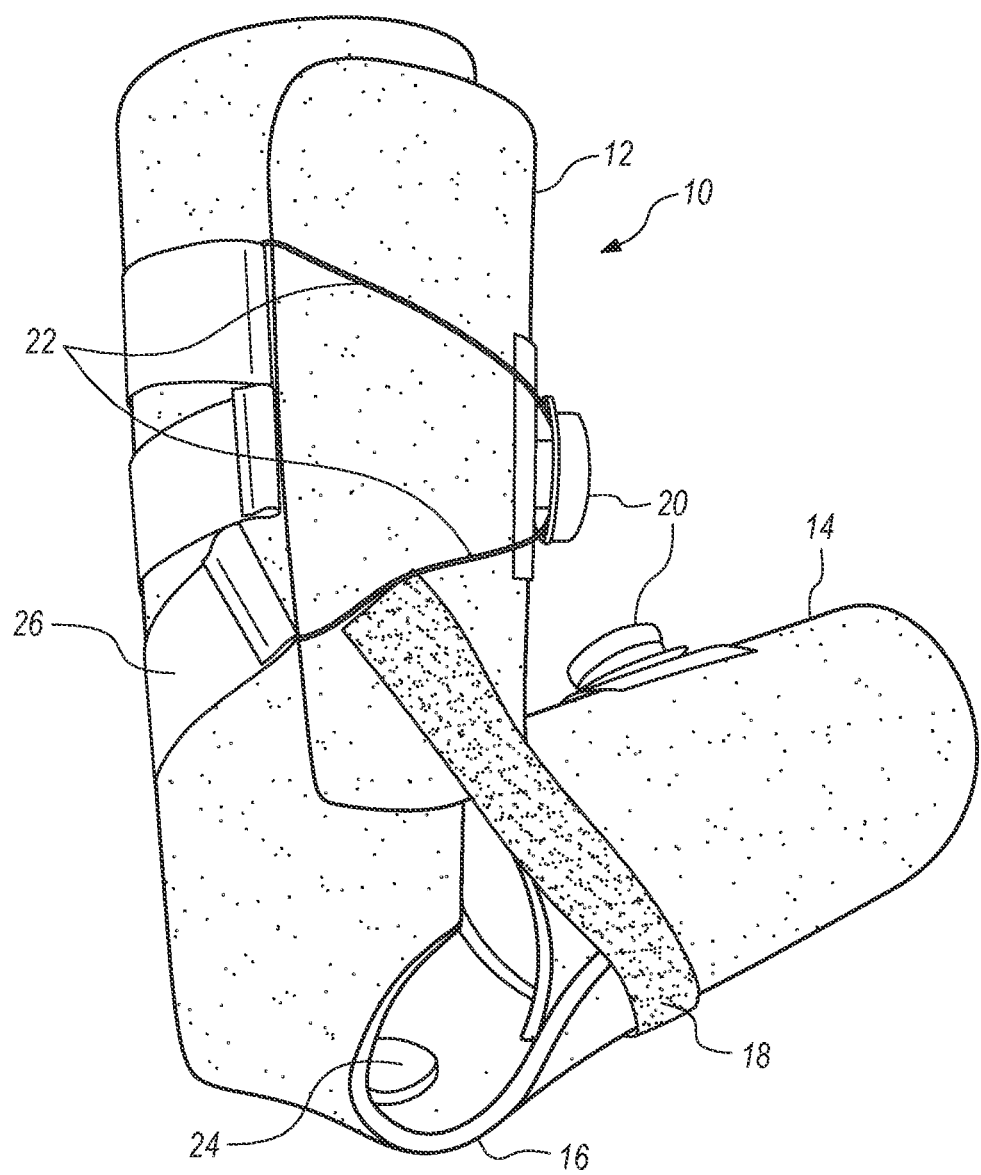
FIG. 3 is a right-rear perspective view of a first embodiment of the present invention.

An elbow brace according to an embodiment of the present invention is shown in FIGS. 1-3. Shell 10 is constructed of a single piece of thermoformable material, such as the Exos® thermoformable composite plastic material offered by DJO, LLC of Lewisville, Texas A material of this type is taught by U.S. Pat. No. 5,645,671, which is incorporated by reference herein. The material is designed to be adjustable and reformable such that it may be conformed to any desired shape with the application of heat, and then provide a solid and rigid structure after cooling. A material such as Exos® is lightweight, waterproof, and relatively easy to clean. As shown in the figures, an upper shell section 12 of shell 10 is bent with respect to the lower shell section 14, with an elbow section 16 between these two sections of shell 10. The angle between upper shell section 12 and lower shell section 14 may be formed as desired by the medical professional applying the device, including as a right angle. As can be seen in the figures, shell 10 is shaped so that the patient's arm is cupped within the thermoformable material of shell 10, with openings at either end and around the sides of the elbow area such that air may easily pass to the patient's skin.

Figure 4:
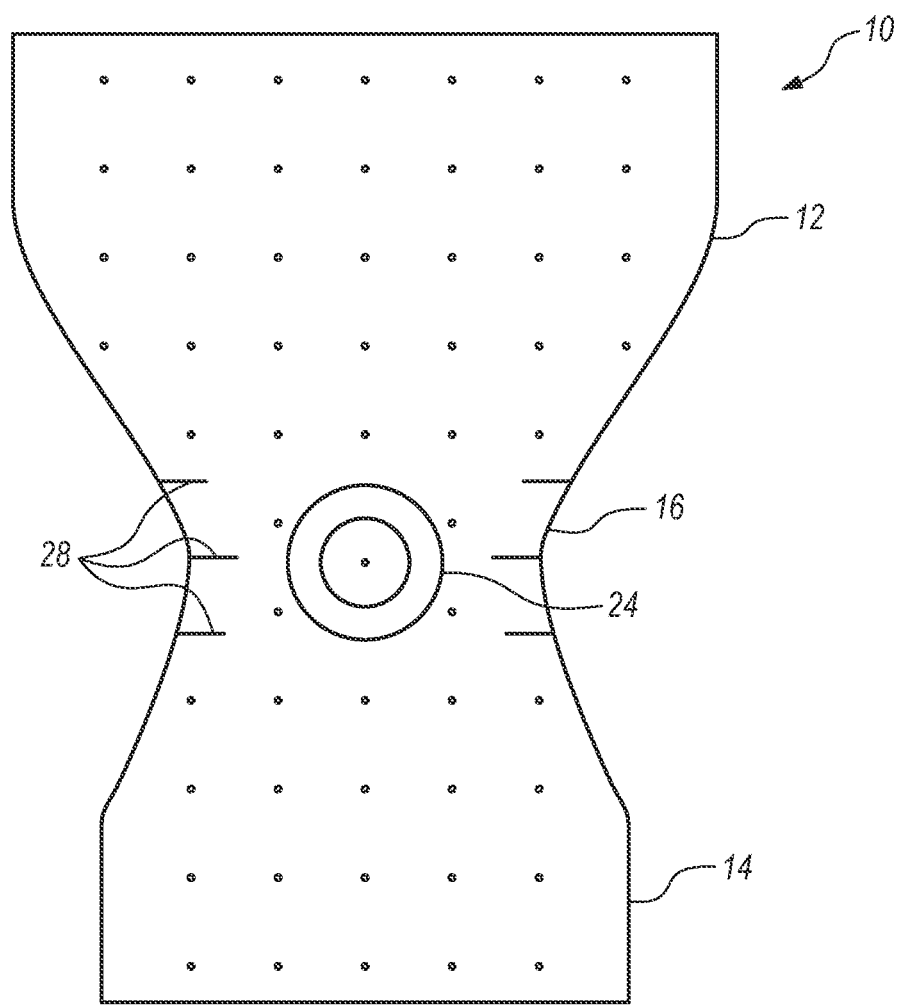
FIG. 4 is a top plan view of a shell and ring pad before forming according to a second embodiment of the present invention.

FIG. 4 depicts shell 10 in an alternative embodiment of the invention, in this case shell 10 shown as a flat piece before forming onto the arm of a patient. In this embodiment, shell 10 includes perforations through its thermoplastic material in order to improve the quantity of air reaching the patient's arm within the brace. Any number and size of perforations may be employed, provided that the rigidity of shell 10 is not compromised thereby. Shell 10 in this embodiment also includes slots 28 which are cut at elbow section 16. The purpose for slots 28 is to ease the formation process by providing relief at the portion of shell 10 that will be subject to the most substantial bending during the forming process. Any number of slots 28 may be including in this embodiment, and the depth of the slots may be modified as desired and as best suits any particular thermoplastic material used for the construction of shell 10.

The angle between upper shell section 12 and lower shell section 14 may be maintained during use while on a patient's arm by means of elbow strap 18. Elbow strap 18 passes from one side of upper shell section 12, under lower shell section 14, and then attaches at the opposite side of upper shell section 12. One or both ends of elbow strap 18 may be attached with hook-and-loop fasteners. One end of elbow strap 18 may be permanently attached with stitching, adhesives, or the like. Because hook-and-loop fasteners may be easily detached and reattached at various positions, elbow straps 18 may be adjusted for length as desired, which may to a limited degree adjust the angle between upper shell section 12 and lower shell section 14.

Upper shell section 12 and lower shell section 14 are formed by curling each of these ends of shell 10 into a roughly round shape around the area where the patient's arm is fitted. These sections 12 and 14 may be held closed around the arm during use by tightening connectors. In the embodiment of the figures, closures 20 that secure and tighten laces 22 extending from anchors 26 serve as the tightening connectors. Closures 20 contain a spool that allows for tightening or loosening of laces 22 by turning closures 20 either clockwise or counterclockwise. Closures 20 may be held to shell 10 by means of hook-and-loop fasteners. Anchors 26 may be attached to shell 10 by adhesives, stitches, or other secure means. Closures such as closures 20 are sold by, for example, BOA® Technology Inc. of Denver, Colorado Such a device is taught by U.S. Pat. No. 11,457,698, which is incorporated herein by reference. These closures are commonly used for sports equipment such as ski boot lacing. Other types of connectors could be used in alternative embodiments of the invention, including, for example, the use of straps or traditional lacing.

Ring pad 24 is attached within shell 10 inside elbow section 16, as seen most clearly in FIG. 1. Ring pad 24 is sized and positioned to receive the point of the patient's elbow when the device is worn. Ring pad 24 may be formed of any compressible yet sturdy material to provide comfort to the patient. Ring pad 24 may be formed of a water-resistant material in order to prevent damage to the device should it be exposed to rain or other sources of moisture. Ring pad 24 may be attached at elbow section 16 with any sufficiently durable adhesive.

To fit the device to the patient, shell 10 begins as a flat piece. Ring pad 24 is attached at elbow section 16 of shell 10. A medical professional bends and curls shell 10 to form upper shell section 12 fitted loosely around the patient's upper arm, while lower shell section 14 is fitted loosely around the patient's lower arm, with the patient's elbow resting comfortably in ring pad 24. Once shell 10 is shaped as desired, elbow strap 18 is pulled into place and secured with the hook-and-loop fasteners. Laces 22 are fitted around closures 20 at both upper shell section 12 and lower shell section 14, and then closures 20 are turned in order to draw these sections of shell 10 down securely but comfortably in place around the patient's arm. When the patient desires to remove the device, closures 20 are loosened so that laces 22 are released, and elbow strap 18 is removed at one or both ends.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. When a grouping is used herein, all individual members of the group and all combinations and subcombinations possible of the group are intended to be individually included. When a range is stated herein, the range is intended to include all subranges and individual points within the range. All references cited herein are hereby incorporated by reference to the extent that there is no inconsistency with the disclosure of this specification.

The present invention has been described with reference to certain preferred and alternative embodiments that are intended to be exemplary only and not limiting to the full scope of the present invention, as set forth in the appended claims.

The invention claimed is:

1. An elbow brace, comprising:
    a shell comprising an upper shell section, a lower shell section, and an elbow section connecting the upper shell section and lower shell section, wherein the upper shell section comprises a first upper shell section side and a second upper shell section side;
    a first tightening connector at the upper shell section;
    a second tightening connector at the lower shell section;
    a ring pad attached inside of the elbow section of the shell; and
    an elbow strap extending from the first upper shell section side to the lower shell section and from the lower shell section to the second upper shell section side.

2. The elbow brace of claim 1, wherein the shell is a formable shell.

3. The elbow brace of claim 2, wherein the formable shell comprises a thermoformable material.

4. The elbow brace of claim 3, wherein the thermoformable material comprises a thermoformable plastic.

5. The elbow brace of claim 1, wherein the elbow strap comprises an elbow strap first end and an elbow strap second end, wherein the elbow strap first end is attached to the first upper shell section side, wherein the elbow strap second end is attached to the second upper shell section side, and wherein one or both of the elbow strap first end and the elbow strap second end are removably attached to the first upper shell section side and second upper shell section side, respectively.

6. The elbow brace of claim 5, wherein the elbow strap comprises a single piece extending from the first upper shell section side, under the lower shell section, and to the second upper shell section side.

7. The elbow brace of claim 6, further comprising an elbow strap hook-and-loop fastener connecting one or both of the elbow strap first end and the elbow strap second end to the first upper shell section side and second upper shell section side, respectively.

8. The elbow brace of claim 1, wherein one or both of the first tightening connector and the second tightening connector comprise at least one lace.

9. The elbow brace of claim 8, wherein one or both of the first tightening connector and the second tightening connector comprise a closure device comprising a spool to receive the at least one lace.

10. The elbow brace of claim 9, wherein one or both of the first tightening connector and the second tightening connector comprise an anchor connected to the at least one lace.

11. The elbow brace of claim 10, further comprising at least one closure device hook-and-loop fastener connecting the at least one closure device to the shell.

12. The elbow brace of claim 1, wherein the ring pad comprises an opening sized to receive a point of a patient's elbow.

13. The elbow brace of claim 12, wherein the ring pad comprises a compressible material.

14. The elbow brace of claim 13, wherein the elbow ring comprises a water-resistant material.

15. The elbow brace of claim 1, wherein the shell comprises a plurality of perforations extending through a thickness of the shell.

16. The elbow brace of claim 1, wherein the elbow section comprises a plurality of slots cut partially across and lateral to the elbow section.

\* \* \* \* \*